(12) United States Patent
Kirchev

(10) Patent No.: US 8,268,148 B2
(45) Date of Patent: Sep. 18, 2012

(54) REFERENCE ELECTRODE, MANUFACTURING METHOD AND BATTERY COMPRISING SAME

(75) Inventor: Angel Zhivkov Kirchev, Aix-les-Bains (FR)

(73) Assignee: Commissariat a l'energie Atomique, Paris (FR)

( * ) Notice: Subject to any disclaimer, the term of this patent is extended or adjusted under 35 U.S.C. 154(b) by 687 days.

(21) Appl. No.: 12/448,623

(22) PCT Filed: Jun. 25, 2007

(86) PCT No.: PCT/IB2007/002752
§ 371 (c)(1), (2), (4) Date: Jun. 26, 2009

(87) PCT Pub. No.: WO2008/090403
PCT Pub. Date: Jul. 31, 2008

(65) Prior Publication Data
US 2010/0086838 A1 Apr. 8, 2010

(30) Foreign Application Priority Data

Jan. 22, 2007 (WO) .................. PCT/IB2007/000813

(51) Int. Cl.
*G01N 27/30* (2006.01)
*G01N 27/36* (2006.01)
*G01N 27/401* (2006.01)

(52) U.S. Cl. .......... 204/435; 29/746; 429/222; 429/223; 429/225; 429/227; 429/235

(58) Field of Classification Search .................. 204/435; 29/746; 429/222, 223, 225, 227, 233, 235
See application file for complete search history.

(56) References Cited

U.S. PATENT DOCUMENTS

| | | | | |
|---|---|---|---|---|
| 3,877,985 A | * | 4/1975 | Rampel | 429/59 |
| 4,645,583 A | | 2/1987 | Shirai et al. | |
| 5,034,113 A | * | 7/1991 | Iwamoto | 204/435 |
| 5,238,553 A | * | 8/1993 | Hettiarachchi et al. | 204/435 |
| 5,833,825 A | * | 11/1998 | Otten et al. | 204/435 |
| 2001/0045357 A1 | * | 11/2001 | Broadley et al. | 204/435 |
| 2002/0011422 A1 | * | 1/2002 | Meier | 205/775 |
| 2005/0133369 A1 | * | 6/2005 | Sovrano et al. | 204/435 |

FOREIGN PATENT DOCUMENTS

| | | |
|---|---|---|
| DE | 195 33 059 A1 | 3/1997 |
| JP | A-59-154350 | 9/1984 |
| JP | A-06-317553 | 11/1994 |
| WO | WO 2004/019022 A1 | 3/2004 |
| WO | WO 2004019022 A1 * | 3/2004 |

* cited by examiner

*Primary Examiner* — Bruce Bell
(74) *Attorney, Agent, or Firm* — Oliff & Berridge, PLC

(57) ABSTRACT

A reference electrode having a casing with an inner cavity successively filled with a paste constituting an active material and a porous material impregnated with an electrolyte solution. The projecting end of a silver wire is embedded in the paste at the bottom of the inner cavity. The paste is constituted of a powder of a silver compound and of the alkaline electrolyte solution. The silver compound is any insoluble silver salt or oxide containing the negative ion of the electrolyte solution. The impregnated porous material is preferably constituted by a plurality of mat separator pieces mechanically and compressed by a closing plug, closing the inner cavity and forming a porous liquid junction.

13 Claims, 9 Drawing Sheets

REFERENCE ELECTRODE, MANUFACTURING METHOD AND BATTERY COMPRISING SAME

BACKGROUND OF THE INVENTION

The invention concerns a reference electrode comprising successively, within an inner cavity of a casing, an active material comprising particles of a silver compound and a porous material impregnated with an electrolyte solution, a silver wire fixed to a bottom of the inner cavity being partially embedded in said active material and said inner cavity being closed by a closing plug forming a porous liquid junction.

STATE OF THE ART

A reference electrode is classically used for measurement of electrode potentials in electrochemical experiments. The reference electrode mainly comprises an electrochemical redox couple, which has a stable potential and the potential of a working electrode of an electrochemical cell is then defined as the voltage difference between the working electrode and the reference electrode.

Known reference electrodes are, for example, normal hydrogen electrodes (redox couple $H^+/H_2$ on platinized platinum), which are however not used frequently in practice since they require special conditions (constant temperature and bubbling with gaseous hydrogen), saturated calomel electrodes ($Hg/Hg_2Cl_2$ in saturated KCl water solution), saturated mercurous sulfate electrodes ($Hg/Hg_2SO_4$ in saturated $K_2SO_4$ water solution), etc.

The reference electrode preferably contains the same electrolyte as the electrochemical cell, both electrolytes being in contact through a salt bridge or a liquid junction, for example through a porous membrane, which maintains the ionic current between the electrolytes, but substantially delays the diffusion of the ions from the electrochemical cell into the reference electrode and vice versa.

The reference electrode usually used in electrochemical cells with alkaline electrolytes in laboratory practice is a commercially available mercury oxide reference electrode Hg/HgO with NaOH or KOH electrolyte. The main drawbacks of this type of reference electrode are its high cost, large size, environmental hazard due to the use of mercury as well as low mechanical strength if the body of the electrode is made of glass. Furthermore, the liquid state of mercury at room temperature leads to additional complications in the construction and the manufacturing of the electrode.

International patent application WO-A-2004/019022 discloses a lead-acid battery with a permanently integrated $Ag/Ag_2SO_4$ reference electrode at least in one of the cells. The reference electrode can thus be used to control the process of charge and/or discharge of the battery as well as to measure the acid density and the state of charge of the battery. Gravitation can lead to leakage of the electrolyte, thus accelerating the diffusion exchange between the reference electrode and the lead-acid battery and reducing the life-time and stability of the electrode. Moreover, the substantial length of the silver wire of this reference electrode leads to relatively high costs.

An $Ag/Ag_2O$ reference electrode for concrete burying is disclosed in Japanese Patent Application JP-A-06317553 to monitor the rate of the corrosion of the steel used to reinforce the concrete. This $Ag/Ag_2O$ redox couple appears to be suitable for a reference electrode for measurements of electrode potentials in alkaline media. However, the known structure is not appropriate for batteries. In particular, the use of wooden plug, cork stopper, gypsum fibrosum and mortar as liquid junction and electrode closure is inappropriate for a reference electrode for battery integration. Moreover, neither the electrolyte ($Ca(OH)_2$) nor the disclosed composition of the active material (mixture of Ag and $Ag_2O$ particles, carbon black and water absorbing polymer gel containing a calcium hydroxide saturated solution) is suitable for battery monitoring applications. More particularly, the low solubility of the calcium hydroxide and the gelling of the electrolyte would lead to a substantial increase of the reference electrode resistance compared to the presently commercially available reference electrodes.

In Japanese Patent Application JP-A-59154350, an $Ag/Ag_2O$ reference electrode is formed by oxidation of the silver surface and no liquid junction is used, i.e. this electrode actually constitutes a pseudo-reference electrode and its potential depends strongly on any variation of the electrolyte composition and concentration.

The availability of low-cost reference electrodes is of great importance in rechargeable batteries (Nickel-Cadmium, Nickel-Metal Hydride, Nickel-Zinc) and alkaline fuel cells (for example with $NaBH_4$ as a fuel material). Such electrochemical power sources can be used in different applications, for example in electric or hybrid vehicles, as photovoltaic storage systems, backup energy systems etc. The large arrays of cells necessary in these applications lead to a high cost of investment for the battery. Thus the requirements in term of duration and maintenance of these energy storage systems are quite high. The use of integrated reference electrodes in these batteries as a sensor and control tool for the electrochemical processes on their positive and negative plates during the charge, discharge, floating and in open circuit could increase the durability and efficiency of the storage systems. Additionally, integrated reference electrodes could be used for the development of more accurate methods for estimation of the state of charge (SOC) and state of health (SOH) of alkaline cells and batteries and state of health of alkaline fuel cells.

OBJECT OF THE INVENTION

The object of the invention is to provide a low cost reference electrode for measurements of electrode potentials in electrochemical experiments as well as suitable for permanent integration in rechargeable batteries and in fuel cells.

According to the invention, this object is achieved by the appended claims and more particularly by the fact that said silver compound is an insoluble silver salt or oxide containing the negative ion of said electrolyte solution, said active material is made of a paste, constituted of a powder of said silver compound and of said electrolyte solution, and said impregnated porous material is mechanically compressed by said closing plug.

Another object of the invention is to provide a method of manufacturing such a reference electrode as well as a battery comprising such a reference electrode.

BRIEF DESCRIPTION OF THE DRAWINGS

Other advantages and features will become more clearly apparent from the following description of particular embodiments of the invention given as non-restrictive examples only and represented in the accompanying drawings, in which.

DESCRIPTION OF PARTICULAR EMBODIMENTS

Figure 1:
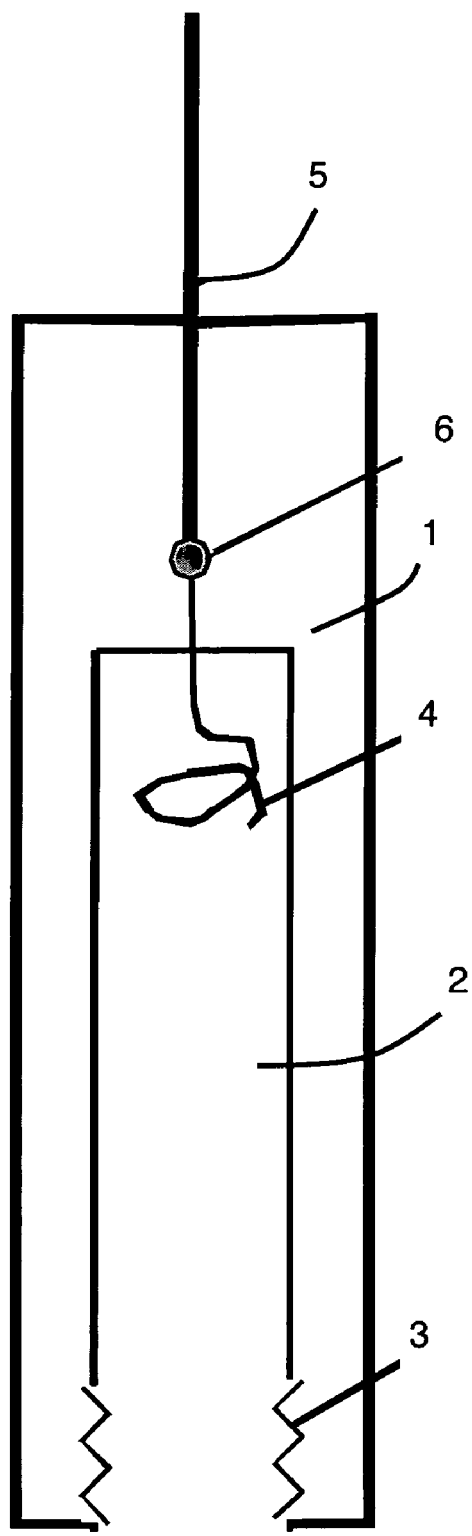
FIG. 1 represents, in cross-section, a hollow body of a reference electrode according to the invention.
Figure 4:
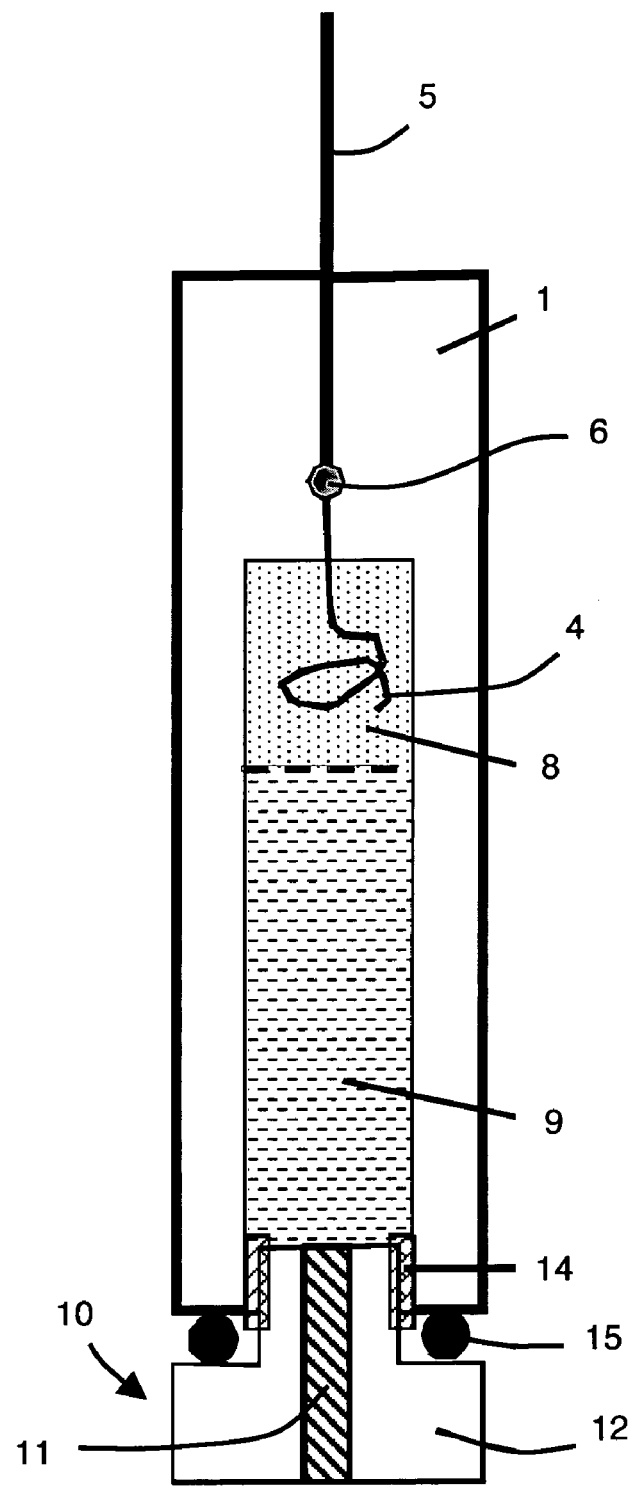
FIGS. 4 and 5 illustrate, in cross-section, two specific embodiments of an assembled reference electrode according to the invention.
Figure 5:
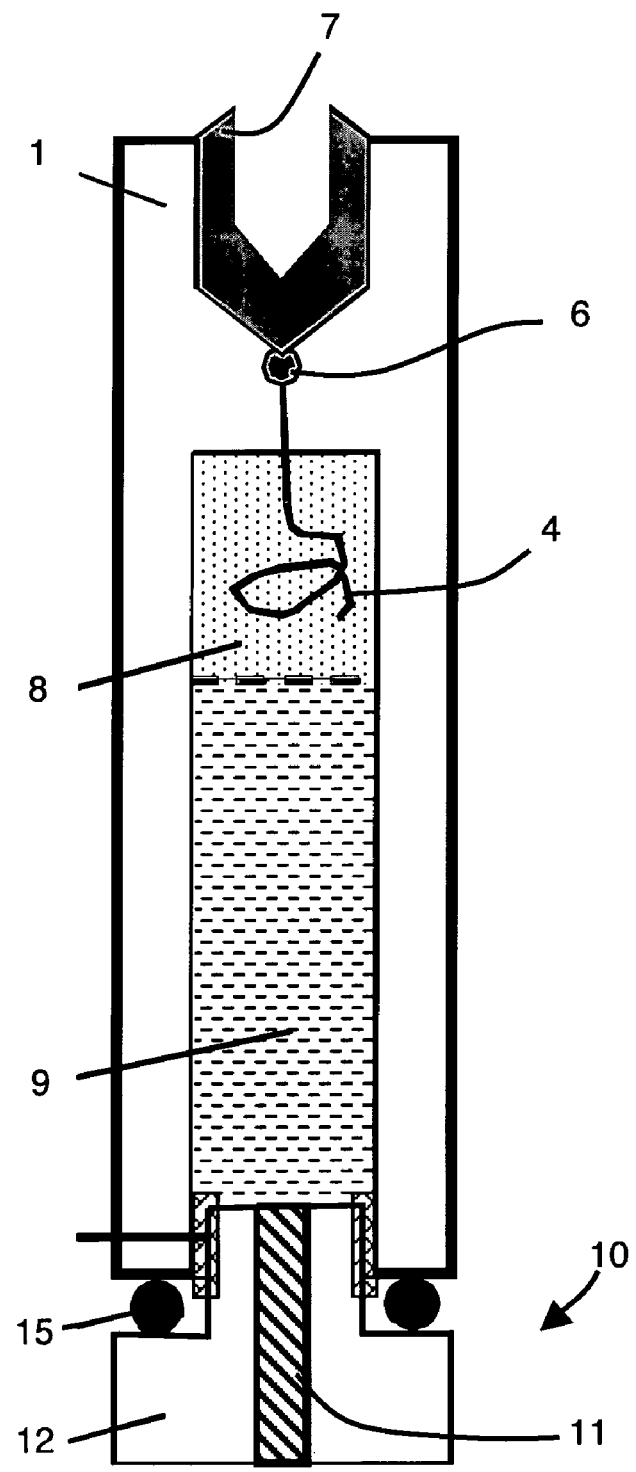

As represented in FIGS. 1, 4 and 5, the reference electrode comprises a casing 1 with an inner cavity 2 having an internally threaded open end 3. Casing 1 is preferably made of any thermoplastic polymer material, that is chemically and physically resistant in concentrated electolyte solutions (for example in alkaline water solutions such as NaOH, KOH or LiOH for an Ag/Ag$_2$O reference electrode), and non-transparent in order to prevent any photochemical reactions leading to decomposition of the silver compound (Ag$_2$O for an Ag/Ag$_2$O reference electrode). Suitable polymers can be polyethylene, polypropylene, PTFE, ABS, polymethylmetacrylate, polystyrene, etc. The outer profile of the casing 1 can be cylindrical or prismatic, depending on the specifications of the future application of the reference electrode. The inner cavity 2 is preferably cylindrical.

A silver wire 4, fixed to the bottom (closed end) of the inner cavity 2, projects into the inner cavity 2. In FIGS. 1 and 4, a first end of the silver wire 4 is embedded in the casing 2 and connected to a plastic-covered connecting cable 5 at a contact point 6 located within the casing at the closed end (upper end in FIGS. 1 and 4) thereof.

In an alternative embodiment illustrated in FIG. 5, the first end of the silver wire 4 is connected at contact point 6 to an electrical connector 7 located in a corresponding outer recess of the closed end of the casing 1. Electrical connector 7 can be of any known type, for example BNC, PIN, banana, screw cap, stereo-jack, etc.

The first end of the silver wire 4 is preferably inserted in the polymer casing 1 during casting of the casing, by means of known corresponding matrix and machine for polymer melting and casting.

The inner cavity 2 of the casing 1 is then preferably filled with a concentrated HNO$_3$ (50% wt.) solution so as to cover the silver wire 4. The nitric acid is left in the inner cavity 2 for 10 min in order to clean chemically the surface of the silver wire 4. Then, the inner cavity 2 is washed with distilled or demineralized water. After washing, the inner space can be dried either rapidly with compressed air or more slowly in a drying oven, for example during 4 h at 60° C. in air atmosphere.

As shown in FIGS. 4 and 5, the inner cavity 2 is then partially filled with an active material, preferably a paste 8, embedding the projecting part of the silver wire 4. In a preferred embodiment, the paste 8 is prepared by mixing a silver compound in powder form, for example Ag$_2$O powder, and an appropriate electrolyte solution in the following ratio:

$$m(\text{silver compound})/V(\text{electrolyte}) = 1.69 \pm 0.05 \text{ g/ml}.$$

The silver compound can be any insoluble silver salt or oxide containing the negative ion of the associated electrolyte solution.

A paste with similar consistency can be prepared with different electrolytes with different concentrations and compositions.

The paste can be deposited on the bottom of the inner cavity 2 by means of a syringe-type device. The paste should fill the whole space of the inner cavity in which the silver wire 4 is located, thus allowing the use of the whole silver surface. In order to minimize the quantity of paste 8 to be used as well as the length of the reference electrode, the projecting part of the silver wire 4 is preferably spirally wounded as shown in FIGS. 1, 4 and 5.

As shown in FIGS. 4 and 5, the remaining cavity is then filled with a porous material 9 impregnated with the electrolyte solution. The electrolyte is thus immobilized in this part of the inner cavity 2 by absorption in the porous material 9.

The porous material 9 is a soft porous material, preferably constituted by a plurality of pieces cut into a mat separator material typically used in the manufacturing of sealed Nickel-Cadmium and Nickel-Metal Hydride rechargeable cells. The absorptive mat separator is preferably cut into pieces having a length of 2-3 mm and a width of 0.5-1 mm. The material of the pieces is then soaked with the electrolyte solution and the inner cavity 2 is filled with the impregnated pieces up to an intermediate section located between two end sections of the internally threaded open end 3 of the casing, i.e. up to slightly over the internal edge of the threaded end 3.

The porous material 9 can also be made of fibers, for example glass, polypropylene or polyethylene fibers.

A closing plug 10, which will be described more in detail latter, is then screwed in the open end of the inner cavity 2, thus compressing the impregnated porous material and closing the inner cavity 2. The quantity of impregnated porous material 9 initially introduced into the inner cavity 2 is such that the volume of the porous material decreases of 4-5% under the force applied by the closing plug. For example, if the length of the inner cavity filled with the impregnated porous material 9 is 50 mm in the assembled reference electrode, i.e. after closing by the closing junction plug 10, this length should be about 52.5 mm before fitting of the closing junction plug 10. The mechanical compression of the impregnated porous material 9 inside the reference electrode will thus ensure long time stability of the ohmic contacts inside the electrode. The use of the absorptive mat separator material can keep this mechanical compression at least for the life time of a rechargeable cell using the same separator material.

The closing junction plug 10 comprises a porous liquid junction body 11 forming the liquid junction between the electrolytes of the reference electrode and of the cell or battery in which the reference electrode is located. The mechanical compression of the impregnated porous material thus also ensures continuous high conductive ionic connection between the porous material of the closing junction plug 10, the immobilized electrolyte of the impregnated porous material 9, the paste 8 constituting the active material and the surface of the silver wire 4. The compression also prevents failure of the electrode quality in systems wherein a lot of mechanical vibrations are occurring, for example in hybrid and electric vehicle applications.

After assembly the reference electrode is preferably placed during 48 h in an electrolyte solution identical to the electrolyte solution used in the reference electrode in order to stabilize its potential.

Figure 2:
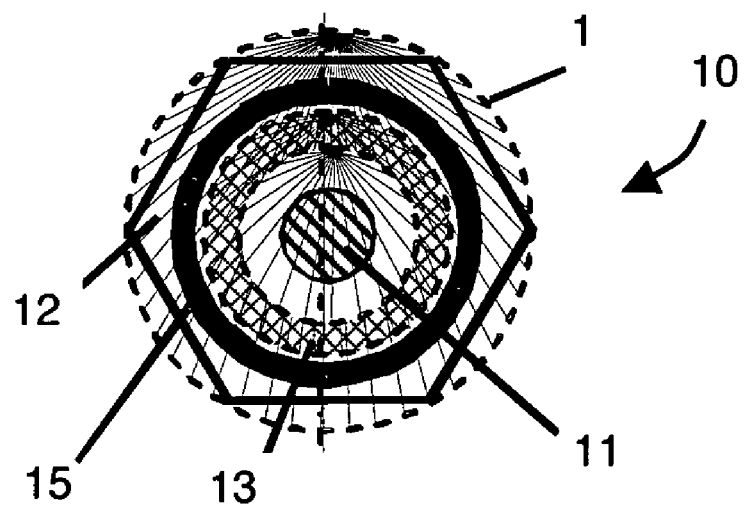
FIGS. 2 and 3 represents a particular embodiment of a closing plug of a reference electrode according to the invention, respectively in top view and in cross-section.
Figure 3:
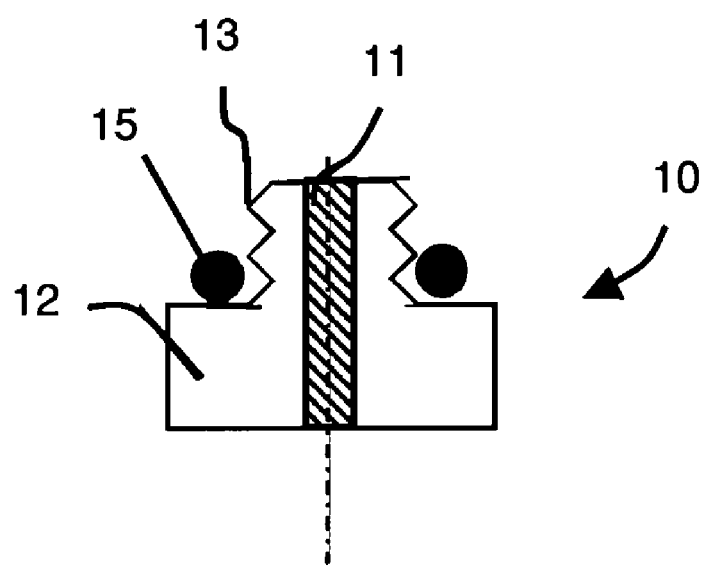

As shown in FIGS. 2 and 3, closing plug 10 preferably comprises a plastic body 12, for example in polymer, surrounding the porous liquid junction body 11. The porous liquid junction body 11 is preferably inserted in the plastic body 12 during casting of the plastic body 12, by means of known corresponding matrix and machine for polymer melting and casting. As casing 1, the plastic body 12 is preferably made of any thermoplastic polymer material that is chemically and physically resistant in concentrated electrolyte solutions (for example NaOH, KOH and LiOH for an $Ag/Ag_2O$ reference electrode or $H_2SO_4$ for an $Ag/Ag_2SO_4$ reference electrode). The porous liquid junction body 11 can be made of different materials resistant in the electrolyte solution. Suitable materials are, for example, porous ceramics, porous Vycor® (a registered trademark of Corning Glass), base-resistant porous glasses or, preferably, graphite. Graphite is particularly appropriate in view of its availability, low cost and good ionic conductance, together with its high porosity. The use of graphite prevents leakage, due to gravitation, of the electrolyte immobilized within porous material 9 and substantially increases the diffusion exchange time between the reference electrode and the battery, thus increasing the lifetime and the stability of the reference electrode.

As shown in FIGS. 2 to 5, the porous liquid junction body 11 of the closing plug 10 is preferably a cylindrical through body surrounded by plastic body 12. In the represented embodiment, closing plug 10 comprises a large head (lower part in FIG. 3) and a thinner shank with an external thread 13 (upper part in FIG. 3), which cooperates with the complementary internally threaded end 3 of casing 1 to form a screw connection 14 (FIGS. 4 and 5). A plastic O-ring 15, made of a soft material resistant to the electrolyte solution, is preferably located around the shank, close to the head, in order to seal the inner cavity 2 of the reference electrode with respect to the electrochemical cell environment.

The head of the closing plug 10 can have different external profile. It can, for example, be round shaped, hexagonal etc. Both surfaces of the closing plug 10 (towards the inner cavity 2 or towards the electrochemical cell) can be flat or have a conical shape. The length of the closing plug 10 is preferably less than 10 mm, because the ohmic resistance of the electrode is proportional to this length. The diameter of the porous liquid junction body 11 is, for example, comprised between 0.3 and 5 mm. The ohmic resistance of the reference electrode being inversely proportional to the square of the diameter of the porous liquid junction body 11, this diameter should be as big as possible. An optimal value of the diameter of the porous liquid junction body 11 when it is made of graphite is about 2 mm±0.5 mm. For miniature reference electrodes, the diameter of the porous liquid junction body 11 can be comprised between 0.3 and 0.5 mm.

The invention is not limited to the use $Ag/Ag_2O$ as redox couple with NaOH, KOH or LiOH based alkaline electrolyte solutions. More particularly, the following redox couples and associated electrolyte could also be used:

Ag/AgCl with KCl, NaCl, LiCl, $CaCl_2$ or HCl water solution electrolyte;

Ag/AgBr with KBr, NaBr, LiBr, $CaBr_2$ or HBr water solution electrolyte;

Ag/AgI with KI, NaI, LiI, $CaI_2$ or HI water solution electrolyte.

$Ag/Ag_2SO_4$ with $H_2SO_4$ as electrolyte.

FIGS. 6 to 15 show that the electrical characteristics of an $Ag/Ag_2O$ reference electrode according to the invention are well suitable for the intended uses.

Figure 6:
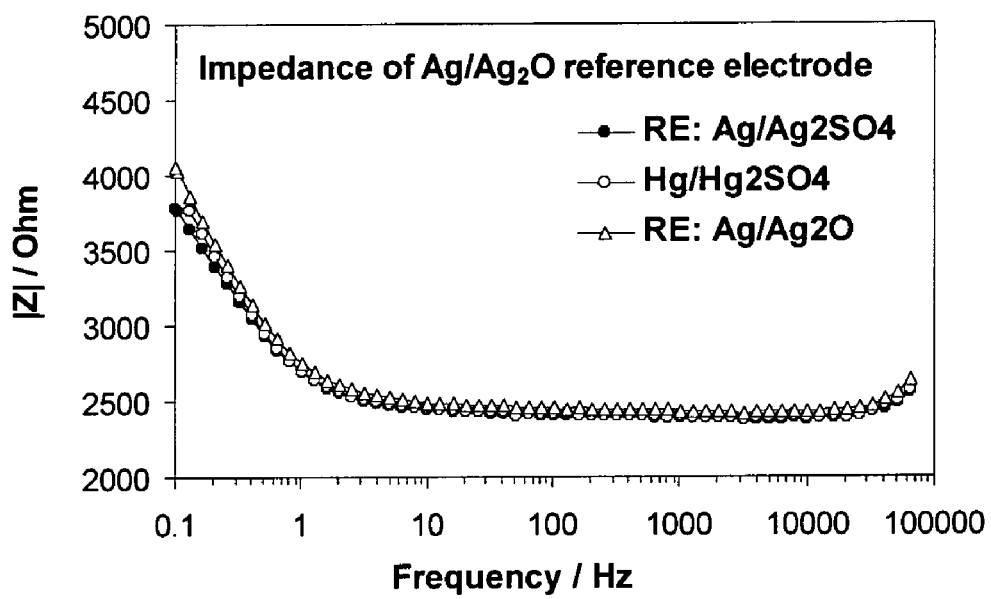
FIGS. 6 and 7 represent the electrochemical module of impedance spectra (Bode plots), i.e. respectively the impedance (FIG. 6) and the phase angle (FIG. 7) versus frequency, of an Ag/Ag$_2$O reference electrode according to the invention and of known Ag/Ag$_2$SO$_4$ and Hg/Hg$_2$SO$_4$ reference electrodes.
Figure 7:
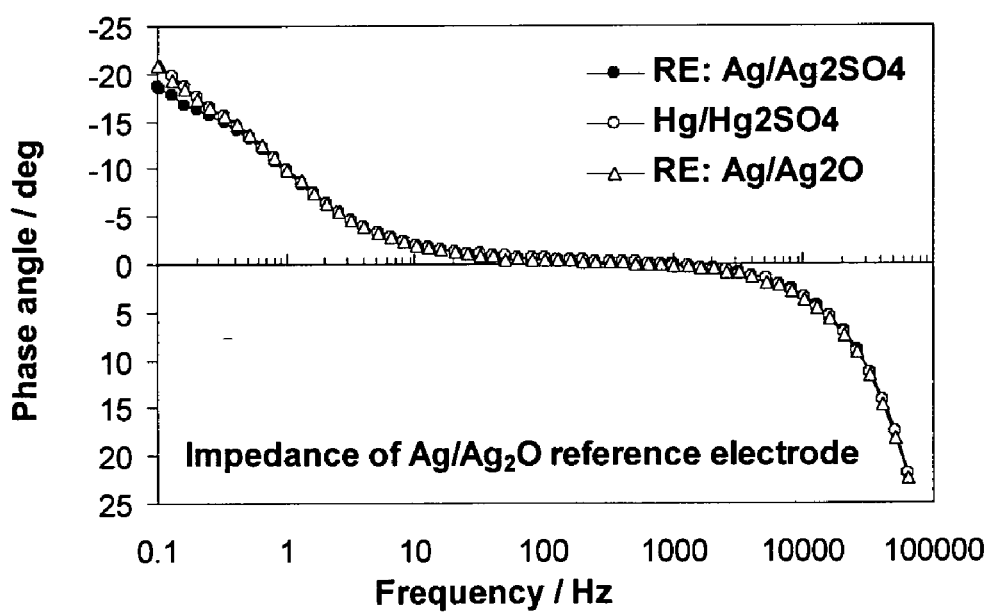

More particularly, FIGS. 6 and 7 show that there is no significant difference between the electrochemical impedance spectra (EIS) of an $Ag/Ag_2O$/5M NaOH reference electrode according to the invention with a graphite junction (length 6 mm, diameter 2 mm) and known $Ag/Ag_2SO_4$/5M $H_2SO_4$ and $Hg/Hg_2SO_4$/5M $H_2SO_4$ reference electrodes. The measurements have been made in three electrodes electrochemical cell in 5M NaOH, using a Pt mesh counter electrode at open circuit, with the different above-mentioned reference electrodes. In all cases, the value of the impedance of the reference electrode is equal or less than 2.5 kΩ in a very large frequency domain, i.e. from 2 Hz to 50 kHz. This is important since a low ohmic resistance of the reference electrode leads to higher noise immunity of the electrochemical measurements. The reference electrode resistance is mainly due to the porous liquid junction and the use of graphite as a liquid junction provides a very effective price-to-performance ratio.

Figure 8:
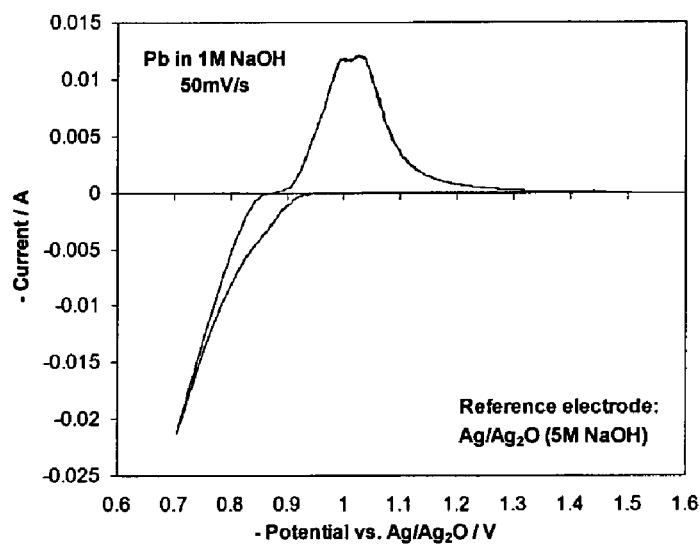
FIGS. 8 and 9 represent cyclic voltammograms of Pb in 1M NaOH, at scan rate 50 mV/s, measured respectively with an Ag/Ag$_2$O reference electrode according to the invention (FIG. 8) and with a known Hg/Hg$_2$SO$_4$ reference electrode (FIG. 9).
Figure 9:
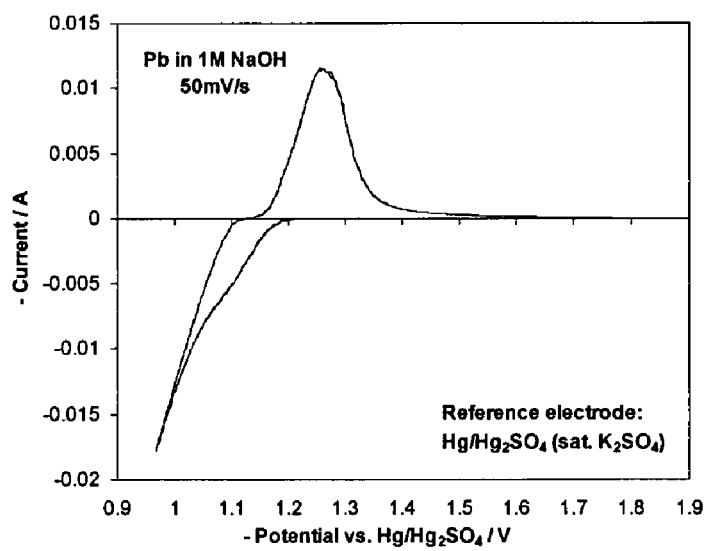

The cyclic voltammograms of FIGS. 8 and 9 show that there is no difference in the noise level during the measurements with the reference electrode according to the invention and with a known reference electrode, so that the reference electrode according to the invention is suitable for electrochemical cyclic voltammetry measurements. In FIG. 8, the scan range is from −1500 to −700 mV and from −1755 to −955 mV in FIG. 9, the potential difference of 255 mV between the two electrodes having been determined preliminary. The coincidence between both voltammograms is almost total and the slight difference in the width of the anodic peak is probably due to a not very good reproducibility of the Pb electrode.

Figure 10:
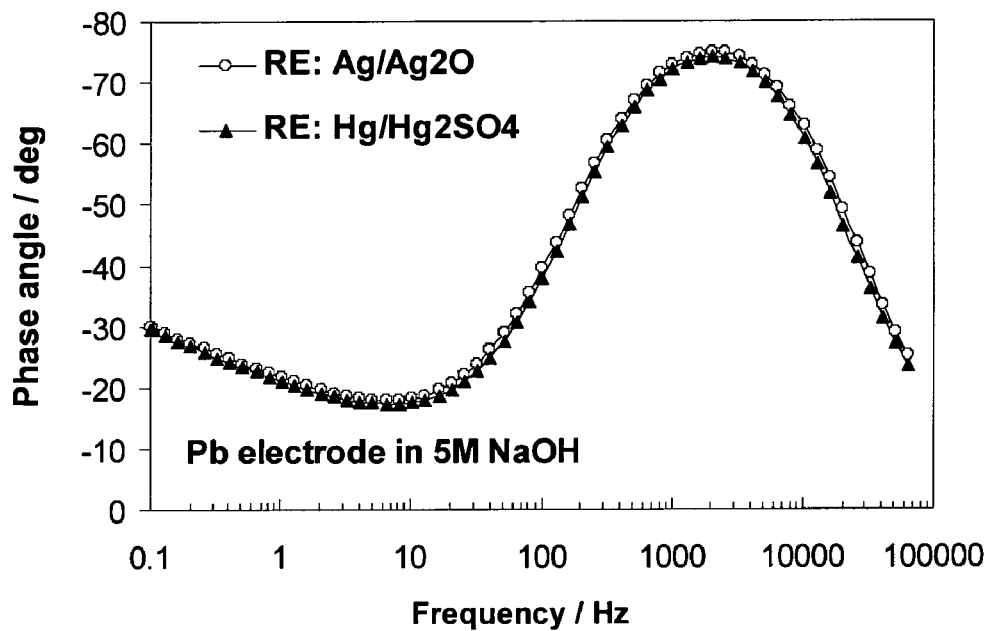
FIGS. 10 and 11 represent the electrochemical impedance spectra (Bode plots) of a Pb electrode immersed in 5M NaOH at open circuit potential, measured respectively with an Ag/Ag$_2$O reference electrode according to the invention and with a known Hg/Hg$_2$SO$_4$ reference electrode.
Figure 11:
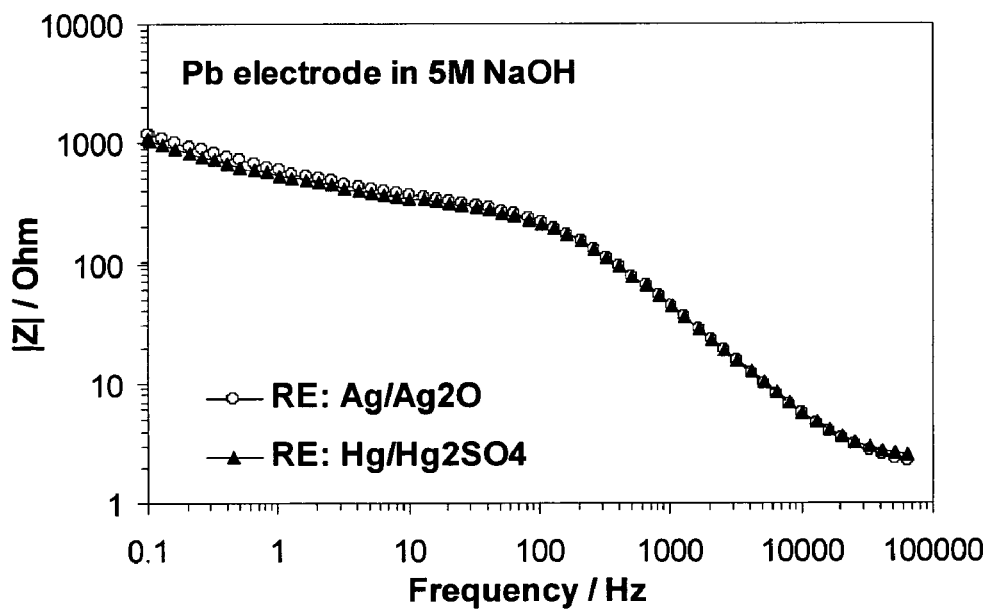

FIGS. 10 and 11 show that there is no significant difference between the electrochemical impedance spectra (EIS) of a Pb electrode immersed in 5M NaOH at open circuit potential, measured with an $Ag/Ag_2O$ reference electrode according to the invention and with a commercially available $Hg/Hg_2SO_4$ reference electrode. Both spectra are noise free. Thus, the $Ag/Ag_2O$ reference electrode according to the invention is suitable for precise electrochemical impedance spectroscopy measurements.

A low cost reference electrode according to the invention can be permanently integrated in a battery comprising at least one cell as well as in fuel cells, for battery monitoring. The electrolyte solutions of the reference electrode and of the battery or fuel cell are then identical.

Figure 12:
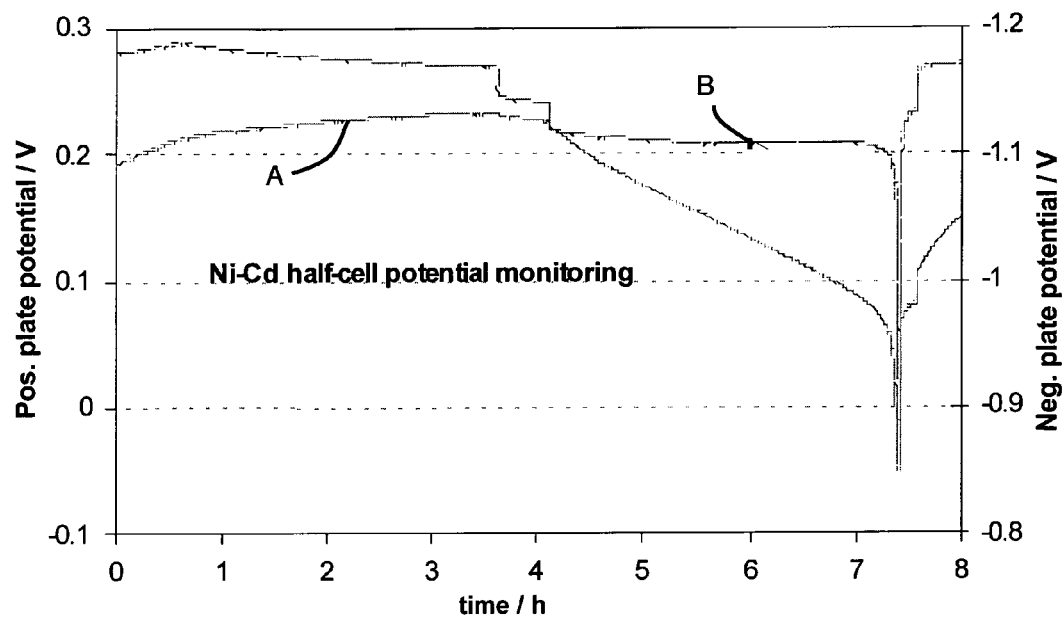
FIG. 12 illustrates the evolution of the positive (curve A) and negative (curve B) electrode potential, measured with an Ag/Ag$_2$O reference electrode according to the invention, during one charge/discharge cycle of 1.6 Ah Nickel-Cadmium rechargeable cell.
Figure 13:
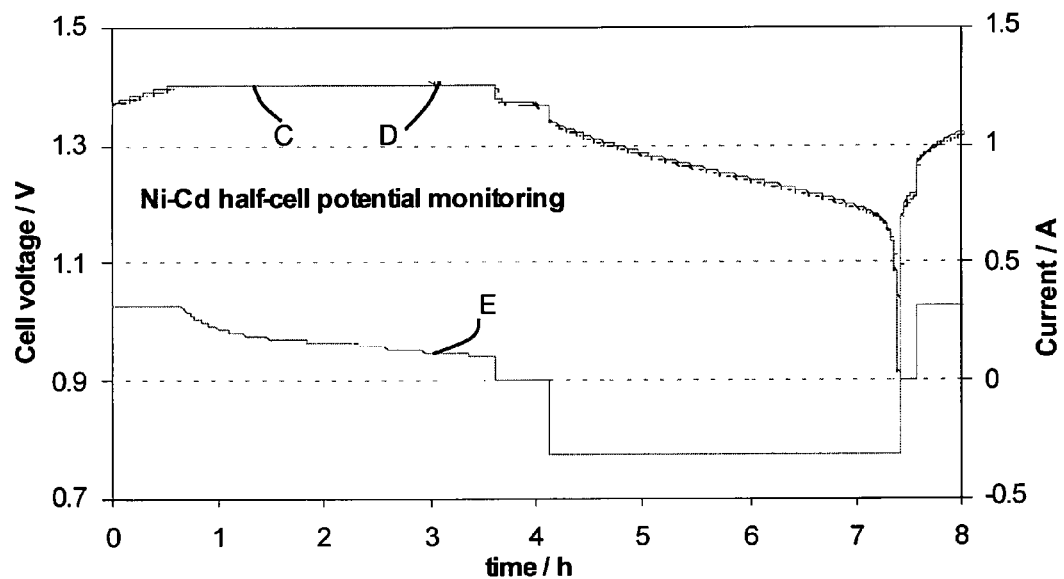
FIG. 13 illustrates, versus time, respectively the cell voltage (curve C), the difference between the positive and the negative electrode potentials (curve D) and the current (curve E) in the same conditions as in FIG. 12.
Figure 14:
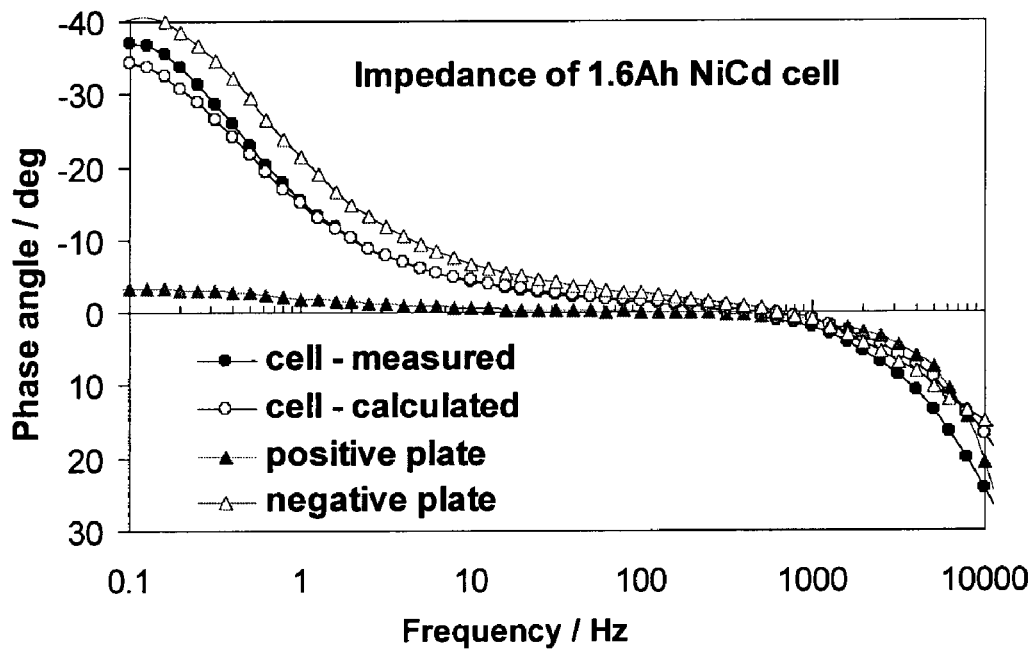
FIGS. 14 and 15 represent the electrochemical impedance spectra (Bode plots), measured with an Ag/Ag$_2$O reference electrode according to the invention, of a 1.6 Ah Nickel-Cadmium rechargeable cell, its positive and negative electrodes and the calculated net impedance from the half-cell impedance data.
Figure 15:
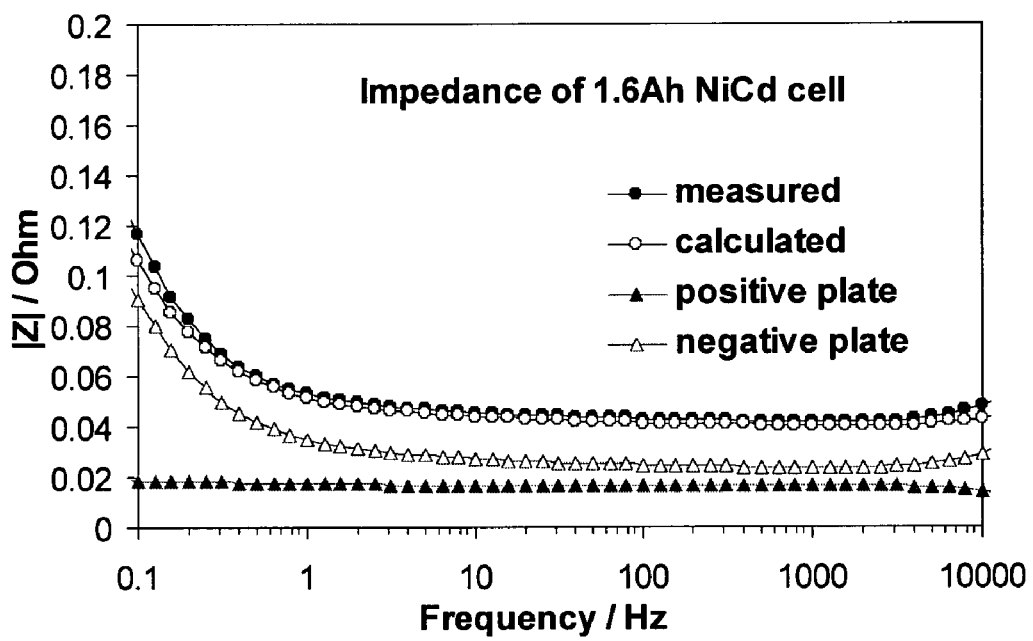

As an example, FIG. 12 illustrates the evolution of the positive and negative electrode potentials measured with an $Ag/Ag_2O$ reference electrode according to the invention during one charge/discharge cycle of a 1.6 Ah Ni—Cd spirally wound rechargeable cell flooded with 5M NaOH at the end of its exploitation period. FIG. 13 illustrates respectively the current (curve E), the measured cell voltage, and the calculated cell voltage obtained by calculating the difference between the positive and the negative electrode potentials, measured independently with respect of the same $Ag/Ag_2O$ reference electrode. The curves C and D of both measured and calculated voltages coincide absolutely, thus showing that the reference electrode according to the invention is suitable for permanent integration in rechargeable cells for monitoring and regulation of its half-cell potentials.

It is also possible to measure the partial impedance of the positive or negative plate of a rechargeable cell with a reference electrode according to the invention. The electrochemical impedance spectra of the above mentioned 1.6 Ah Ni—Cd rechargeable cell illustrated in FIGS. 14 and 15 have been respectively calculated and measured with an $Ag/Ag_2O$ reference electrode according to the invention, at open circuit conditions after 24 h rest period. The calculated cell impedance has been obtained using the following relations:

$$Z'_{cell}=Z'_{pos}+Z'_{neg} \text{(real part of the impedance)}$$

$$Z''_{cell}=Z''_{pos}+Z''_{neg} \text{(imaginary part of the impedance)}$$

i.e. the positive and negative plates are considered to be connected in series. The results are noise-free and both types of cell impedance spectra coincide well.

The integration of the reference electrode according to the invention in a rechargeable cell can be done by its incorporation in the top or in the side wall of a cell, in the valve-plug of the cell for valve-regulated cells or in the cap of the cell in the case of flooded cells.

The invention claimed is:

1. Reference electrode comprising successively, within an inner cavity of a casing, an active material comprising particles of a silver compound and a porous material impregnated with an electrolyte solution, a silver wire fixed to a bottom of the inner cavity being partially embedded in said active material and said inner cavity being closed by a closing plug forming a porous liquid junction, electrode wherein said silver compound is an insoluble silver salt or oxide containing the negative ion of said electrolyte solution, said active material is made of a paste, constituted of a powder of said silver compound and of said electrolyte solution, and said impregnated porous material is mechanically compressed by said closing plug.

2. Electrode according to claim 1, wherein said impregnated porous material is constituted by a plurality of mat separator pieces.

3. Electrode according to claim 1, wherein said impregnated porous material is made of glass, polypropylene or polyethylene fibers.

4. Electrode according to claim 1, wherein said inner cavity comprises an internally threaded open end screwed on a complementary thread of the closing plug.

5. Electrode according to claim 1, wherein said embedded part of the silver wire is spirally wounded.

6. Electrode according to claim 1, wherein said closing plug comprises a plastic body surrounding a porous liquid junction body.

7. Electrode according to claim 6, wherein said porous liquid junction body is made of graphite.

8. Electrode according to claim 1, wherein said electrolyte is an alkaline electrolyte, and said silver compound is chosen among $Ag_2O$, AgCl, AgBr and AgI.

9. Electrode according to claim 1, wherein said electrolyte is $H_2SO_4$, and said silver compound is $Ag_2SO_4$.

10. Method of manufacturing a reference electrode according to claim 1, wherein said inner cavity comprises an internally threaded open end, and said method comprises:
    deposition of the paste, around a projecting end of the silver wire, in the inner cavity of the casing,
    filling the remaining cavity with said porous material, soaked with the electrolyte solution, up to an intermediate section located between two end sections of said internally threaded open end, and
    screwing the closing plug at said open end of the inner cavity for compressing the impregnated mat separator pieces and closing the inner cavity.

11. Method according to claim 10, wherein said impregnated porous material is compressed by 4 to 5% in volume by the closing plug after closing of the inner cavity.

12. Method according to claim 10, wherein said paste is obtained by mixing said silver compound powder with said electrolyte solution in a ratio of 1.69±0.05 g of silver compound per milliliter of electrolyte.

13. Battery comprising a reference electrode according to claim 1, wherein said electrolyte solution of the reference electrode is the same as an electrolyte solution of the battery.

* * * * *